United States Patent [19]

Miyamoto

[11] Patent Number: 5,465,114
[45] Date of Patent: Nov. 7, 1995

[54] BIOLOGICAL SAMPLE OBSERVATION SYSTEM USING A TEMPERATURE CONTROLLED SOLID STATE SENSOR

[75] Inventor: Shigeyuki Miyamoto, Tokyo, Japan

[73] Assignee: NEC Corporation, Japan

[21] Appl. No.: 17,641

[22] Filed: Feb. 12, 1993

[30] Foreign Application Priority Data

Feb. 12, 1992 [JP] Japan .................................. 4-057234

[51] Int. Cl.⁶ ..................................................... H04N 7/18
[52] U.S. Cl. ....................................................... 348/80
[58] Field of Search ........................ 358/93, 107, 213.16, 358/213.11, 213.19, 220; 348/80, 79, 61, 244, 243, 294

[56] References Cited

U.S. PATENT DOCUMENTS

| | | | |
|---|---|---|---|
| 4,551,760 | 11/1985 | Bendell ............................... | 358/213.16 |
| 4,587,563 | 5/1986 | Bendell et al. ...................... | 358/213.16 |
| 4,777,525 | 10/1988 | Preston, Jr. ......................... | 358/93 |
| 5,065,029 | 11/1991 | Krivanek ............................ | 358/213.16 |
| 5,216,500 | 6/1993 | Krummey et al. .......................... | 358/93 |
| 5,307,161 | 4/1994 | Miyamoto ................................ | 348/79 |

FOREIGN PATENT DOCUMENTS

| | | | |
|---|---|---|---|
| 0508828 | 10/1992 | European Pat. Off. ....... | G01N 21/01 |
| 4316478 | 11/1992 | Japan .............................. | G01N 27/26 |

*Primary Examiner*—Tommy P. Chin
*Assistant Examiner*—Bryan S. Tung
*Attorney, Agent, or Firm*—Laff, Whitesel, Conte & Saret, Ltd.

[57] ABSTRACT

In a system and a method for observing a biological sample, a drive unit is connected to a solid state image sensor located to directly observe a biological sample. A record and display unit is connected to the drive unit for receiving, through the drive unit, observed image information picked up by the solid state image sensor. A control unit is connected to the drive unit and the record and display unit for intermittently or periodically putting the solid state image sensor into an operating condition. Thus, it is possible to effectively suppress or prevent the temperature elevation of the biological sample, which would otherwise be caused by the heat generated from the solid state image sensor. Accordingly, it is possible to continuously observe the growth or reproduction of a biological sample for a long time while giving no adverse influence to the growth or reproduction of the biological sample.

9 Claims, 7 Drawing Sheets

BIOLOGICAL SAMPLE OBSERVATION SYSTEM USING A TEMPERATURE CONTROLLED SOLID STATE SENSOR

BACKGROUND OF THE INVENTION

1. Field of the invention

The present invention relates to a method and a system for observing a biological sample.

2. Description of Related Art

Continuous observation of the change in growth over time of the bacterium is useful in medicine bacterium is very convenient from various viewpoints of medicine, pharmacology, agriculture and biology; because continuous observation makes it possible to obtain more information than that obtained in interval observation. In order to continuously observe the change over time of the biological samples, while maintaining a contact temperature, moisture and concentration of carbon dioxide in the sample, it has been necessary to assemble a recording means such as a video camera on a biological microscope and to install a thermostat, a hygrostat and a carbon dioxide gas supplying device on a sample stage of the microscope. This biological sample observation system has been disadvantageous in that various conditions such as the temperature can vary, and therefore, it is difficult to create on the sample stage the same condition as that realized in an incubator.

In order to overcome the above mentioned disadvantage, the applicant proposed a biological sample observation system using a solid state image sensor, in Japanese Patent Application No. 106471/1991 filed on Apr. 4, 1991, which was laid open on Nov. 6, 1992 under Japanese Patent Laid-open Publication No. Hei 4-316478, and which has a corresponding EPC application No. 92 303 257 laid open under Publication EP-A2-508828 on Oct. 14, 1992 and a corresponding U.S. patent application Ser. No. 07/866,008, contents of which are incorporated herein by this reference.

In the proposed biological sample observation system, a sample, holder has a solid state image sensor accommodated in the bottom recessed portion of the sample holder, and the sample is located in and supported by the sample holder in such a manner that the portion of the sample to be observed is positioned just above a photoreception face of the solid state image sensor with no magnifying optical lens interposed between the sample and the solid state image sensor. A filter and a light source are located above the sample, so that light emitted from the light source is irradiated through the filter and then to the sample and then to the photoreception face of the solid state image sensor. The solid state image sensor is driven by a drive unit, and image information is transferred from the solid state image sensor through the driving circuit to a record and display unit, so that an observed sample image is displayed and recorded.

In the above mentioned biological sample observation system, the part excluding the drive unit and the record and display unit is very small in size and can sustain a high temperature and a high moisture. Therefore, the part excluding the drive unit and the record and display unit can be located within an incubator which allows the temperature, the moisture and the concentration of gas such as carbon dioxide to be maintained at a constant. Accordingly, it is possible to make a continuous observation of change with time of a biological sample under a preferred temperature, moisture and concentration of gas.

In the above mentioned biological sample observation system, however, the solid state image sensor and the light source have been continuously and ceaselessly energized during a period in which the sample is being observed. Therefore, if the observation is continued for a long period of time in this biological sample observation system, the heat emitted from the solid state image sensor and the light source will gradually elevate the temperature of the sample. The temperature elevation of the sample gives an adverse affect to the growth of sample cells or to the reproduction of sample fungi or sample bacterium. Therefore, in the above mentioned biological sample observation system, it has been difficult to continuously observe the sample for a long period of time as it is with no adverse influence to the biological sample.

SUMMARY OF THE INVENTION

Accordingly it is an object of the present invention to provide a biological sample observation method and system which have overcome the above mentioned defects of the conventional method and system.

Another object of the present invention is to provide a biological sample observation method and system which the influence of the heat generated from the solid state image sensor and/or the light source is minimized, thereby making it possible to continuously observe a biological sample for a long period of time as it is, with no adverse influence to the biological sample.

The above and other objects of the present invention are achieved in accordance with the present invention employing a biological sample observation system comprising a holding member in the form of a housing having a recess portion and a solid state, image sensor located in the recess portion, the holding member being configured to directly receive an object to be observed above a photoreception face of the solid state image sensor with no optical system between the object to be observed and the photoreception face of the solid state image sensor; a light source located in the holding member for radiating light toward the photoreception face of the solid state image sensor through the object to be observed; a drive unit connected to the solid state image sensor for driving the solid state image sensor; a record and display unit connected to the drive unit for receiving through the drive unit an observed image information picked up by the solid state image sensor; and a control unit connected to at least the drive unit for intermittently or periodically putting the solid state image sensor into an operating condition.

In one embodiment of the biological sample observation system, the control unit is also connected to the light source for intermittently or periodically putting the light source and the solid state image sensor into an operating condition.

Another embodiment of the biological sample observation system also includes a temperature sensor for measuring the temperature of the sample to be observed or the solid state image sensor, the control unit being connected to the temperature sensor for controlling operation of at least the drive unit on the basis of an output of the temperature sensor.

According to another aspect of the present invention, there is provided a method for observing a biological sample using a sample holding member in the form of a housing having a recessed portion and a solid state image sensor located in the recessed portion, the holding member being configured to directly receive a biological sample to be observed above a photoreception face of the solid state image sensor with no magnifying optical lens between the biological sample to be observed and the photoreception face of the solid state image sensor; the method repeating a unitary observation process including the steps of driving the solid state image sensor, starting to record an output of the solid state image sensor simultaneously or after lapse of a first predetermined period of time, stopping the record of the output of the solid state image sensor after lapse of a second predetermined period of time, stopping the driving of the solid state image sensor simultaneously or after lapse of a third predetermined period of time, and allowing a fourth predetermined period of time to elapse.

In one embodiment of the method for observing the biological sample, when the solid state image sensor is driven, a light is irradiated onto the photoreception face of the solid state image sensor simultaneously or after lapse of a fifth predetermined period of time, and when the driving of the solid state image sensor is stopped, the irradiation of the light onto the photoreception face of the solid state image sensor is stopped simultaneously or after lapse of a sixth predetermined period of time.

According to still another aspect of the present invention, there is provided a method for observing a biological sample using a sample holding member in the form of a housing having a recessed portion and a solid state image sensor located in the recessed portion, the holding member being configured to directly receive a biological sample to be observed above a photoreception face of the solid state image sensor with no magnifying optical lens between the biological sample to be observed and the photoreception face of the solid state image sensor; the method repeating a unitary observation process including the steps of driving the solid state image sensor when a temperature of the biological sample to be observed or the photoreception face of the solid state image sensor is not greater than a predetermined reference temperature starting to record an output of the solid state image sensor simultaneously or after lapse of a first predetermined period of time, stopping the record of the output of the solid state image sensor after lapse of a second predetermined period of time, and stopping the driving of the solid state image sensor simultaneously or after lapse of a third predetermined period of time.

As will be apparent from the above, the control unit for controlling the operation of the solid state image sensor is provided in accordance with the present invention, so that the driving of the solid state image sensor is intermittently or periodically stopped in the course of the continuous observation of the sample. If the solid state image sensor is periodically driven at such constant intervals that the heat generated from the solid state image sensor is not accumulated in the sample, a continuous observation of a long time can be performed with a reduced heat influence to the biological sample.

In addition, if the light source is intermittently energized in synchronism with the driving of the solid state image sensor, the heat generation of the light source is suppressed, and therefore, a long continuous observation can be performed with a minimized heat influence to the biological sample.

Furthermore, if the temperature sensor is provided for measuring the heat generated by the solid state image sensor and the measured temperature is fed back into the timing control of the driving of the solid state image sensor, the elevation of the sample temperature is suppressed or prevented, and therefore, a long continuous observation can more easily be performed with no heat influence to the biological sample.

In addition, when the solid state image sensor is out of operation, it is not necessary to record and display the observed image, Accordingly, if the record and display unit is driven in time with the operation of the solid state image sensor, an excellent observed image can be obtained.

The above and other objects, features and advantages of the present invention will be apparent from the following description of preferred embodiments of the invention with reference to the accompanying drawings.

DESCRIPTION OF THE PREFERRED EMBODIMENTS

Figure 1:
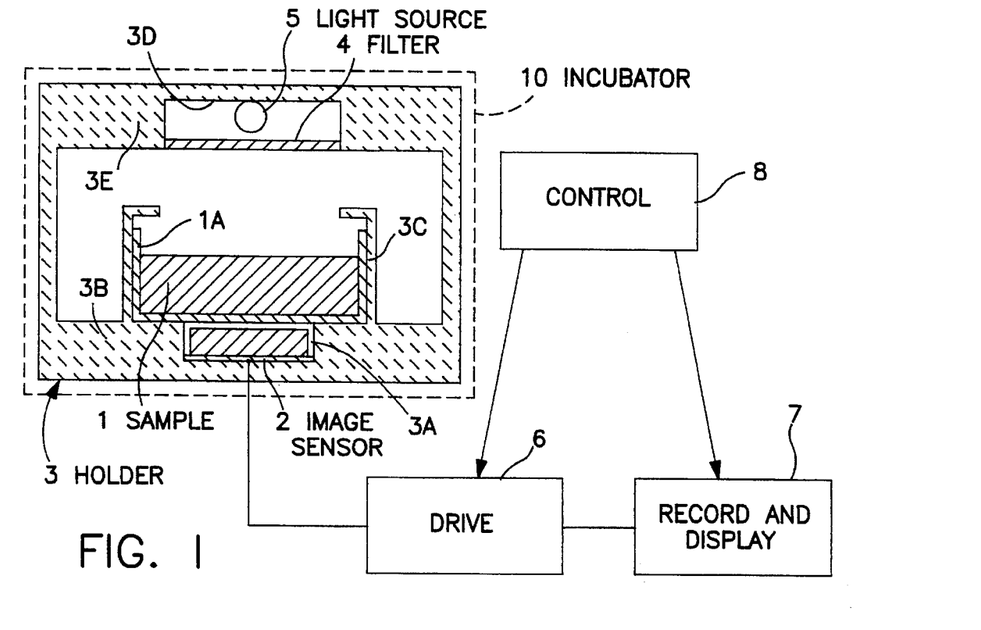
FIG. 1 is a block diagram of a first embodiment of the biological sample observation system in accordance with the present invention.

Referring to FIG. 1, there is shown a block diagram of a first embodiment of the biological sample observation system in accordance with the present invention. The shown system includes a sample holder 3 which can be located, if desired in an incubator 10 conceptually shown by a dotted line in FIG. 1. The sample holder 3 is in the form of a closed housing having one or more communication holes (not shown) allowing an internal space of the sample holder 3 to communicate with an internal space of the incubator 10 when the sample holder 3 is located within the incubator 10 so that the internal space of the sample holder 3 is maintained at the same condition (including the temperature, the moisture and the composition and concentration of gas) as that of the internal space of the incubator 10.

The sample holder 3 has a two-dimensional solid state image sensor 2 accommodated in a recessed portion 3A formed on the bottom plate 3B of the sample holder. The sample holder 3 also has at least three holding arms 3C extending vertically upward from the bottom plate 3B of the sample holder at positions surrounding the recess portion 3A. A small transparent vessel 1A accommodating therein a biological sample 1 to be observed (for example, a medium which cultured cells, fungi and bacterium are located) is positioned just above a photoreception face of the solid state image sensor 2 and held by holding arms 3C, with no magnifying optical lens interposed between the sample 1 and the solid state image sensor 2.

The sample holder 3 has another recessed portion 3D which is formed in a lid plate 3E of the sample holder 3 and which is open toward the image sensor 2. A light source 5 is mounted within the recess portion 3D, and the recess portion 3D is closed or covered with a filter 4 so that a light emitted from the light source 5 passes through the filter 4 and also through the sample 1 so as to inject to the photoreception face of the solid state image sensor 2.

The solid slate image sensor 2 is driven by a drive unit 6, and image information is transferred from the solid state image sensor 2 through the drive unit 6 to a record and display unit 7, so that an observed sample image is displayed and recorded in the record and display unit 7. The drive unit 6 and the record and display unit 7 are connected to a control unit 8, so that the operation of the drive unit 6 and the record unit 8, and hence the operation of the solid state image sensor 2 are controlled by the control unit 8.

With this arrangement, during a continuous observation of the sample 1, the driving of the solid state image sensor 2 can be intermittently stopped by the control unit 8, and therefore, generation of heat from the solid state image sensor 2 which is a main heat generation source can be suppressed, so that it becomes possible to perform a long continuous observation.

In the first embodiment, the light source 5 is ceaselessly maintained during an energized condition in the process of the long continuous observation, and therefore, there is a possibility that the temperature elevation of sample 1 is caused by the heat generated from the light source 1. However, if a sufficient distance is ensured between the light source 5 and the sample 1, or if a light emitting diode, or the like, which has less generation of heat is used as the light source, or if a filter which does not allow infrared light to pass is used for the filter 4, or if the long continuous observation is performed to such an extent that sample 1 does not show a remarkable temperature elevation due to the heat generated from the light source, the heat generated from the light source 1 does not give an adverse influence to the sample. Under these conditions, since the system of the first embodiment is very simple in construction and excellent desirable in size and easy to maintain the first embodiment is very convenient.

Figure 2:
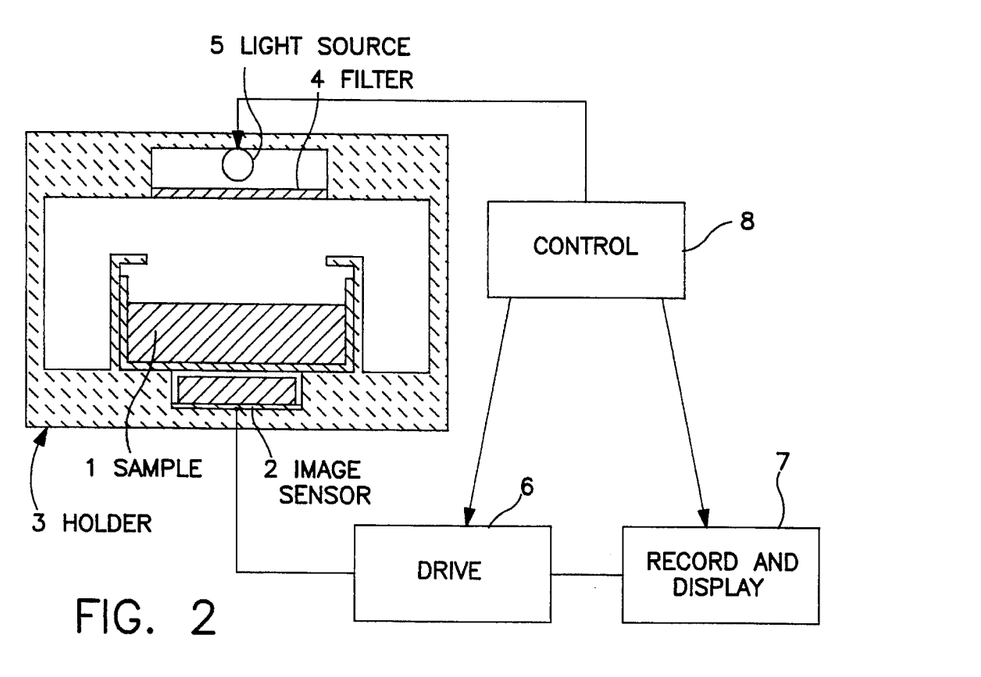
FIG. 2 is a block diagram of a second embodiment of the biological sample observation system in accordance with the present invention.

Referring to FIG. 2, there is shown a block diagram of a second embodiment of the biological sample observation system in accordance with the present invention. In FIG. 2, elements similar or corresponding to those shown in FIG. 1 are given the same reference numerals, and explanation thereof will be omitted.

As will be noted from making a comparison between FIGS. 1 and 2, the second embodiment is different from the first embodiment in that the drive unit 6, the record and display unit 7, and source 5 are all connected to the control unit 8, so that the operation of the light source 5, the drive unit 6 and the record and display unit 7 are controlled by the control unit 8.

Accordingly, in the second embodiment, the driving of the solid state image sensor 2 and the energization of the light source 5 can be intermittently stopped by the control unit 8 in a continuous observation of sample 1, and therefore, generation of heat from the solid state image sensor 2 and the light source 5 can be effectively suppressed, so that it becomes possible to perform a continuous observation without giving adverse thermal influence to sample 1 for a third longer time than that which can be performed in the first embodiment.

Figure 3:
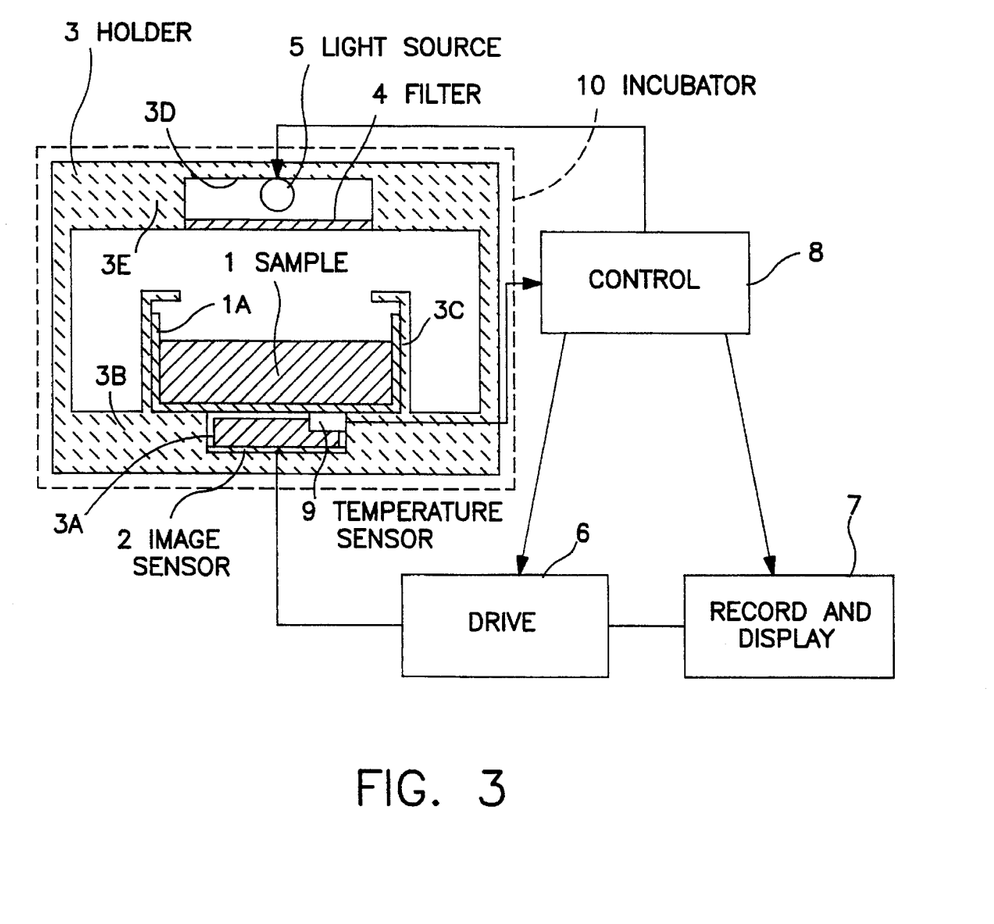
FIG. 3 is a block diagram of a third embodiment of the biological sample observation system in accordance with the present invention.

Referring to FIG. 3, there is shown a block diagram of a third embodiment of the biological sample observation system in accordance with the present invention. In FIG. 3, elements similar or corresponding to those shown in FIGS. 1 and 2 are given the same reference numerals, and explanation thereof will be omitted.

The third embodiment includes a temperature sensor 9 added to the second embodiment for the purpose of measuring the temperature of the sample 1 or the photoreception face of the solid state image sensor 2. An output of the temperature sensor 9 is connected to the control unit 8.

With this arrangement, the control unit 8 can control the operation of the drive unit 6 and the record and display unit 7, and also the light source 5, while monitoring the output of the temperature sensor 9. Accordingly, the third embodiment comprises a feedback system in which the solid state image sensor 2 can be intermittently driven with reference to the output of the temperature sensor 9 during a continuous observation of sample 1, and therefore, the temperature elevation of sample 1 can be prevented. Accordingly, it becomes possible to perform a longer continuous observation without giving adverse thermal influence to sample 1.

Of course, the light source 5 is intermittently energized by the control unit. 8 in synchronism with or with a limited advanced time from the driving of the solid state image sensor 2.

Preferably, the temperature sensor 9 is positioned within sample 1 so as to measure the temperature of sample 1 itself. However, if it is difficult to position the temperature sensor 9 within sample 1, the temperature sensor 9 can be located in the recessed portion 3A of the bottom plate 3B of the sample holder 3, near the photoreception face of the solid state image sensor 2, for the purpose of measuring the temperature of the photoreception face of the solid state image sensor 2. In this case, the elevation in temperature of sample 1 can be estimated from the temperature of the photoreception face of the solid state image sensor 2, or the temperature of the photoreception face of the solid state image sensor 2 can be regarded as being the same as the temperature of sample 1.

Figure 4:
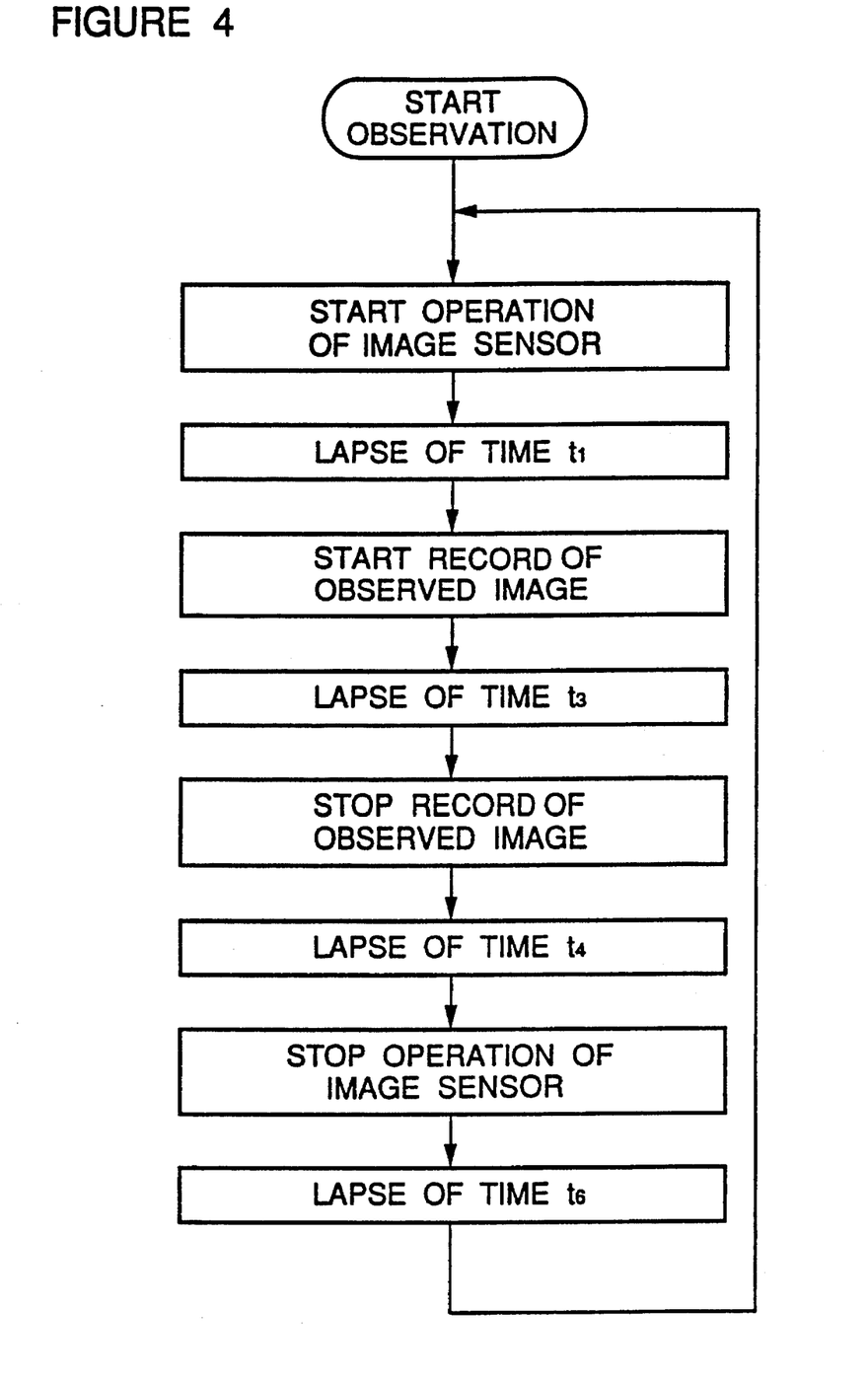
FIG. 4 is a flow chart of a first embodiment of the biological sample observation method in accordance with the present invention.

Referring to FIG. 4, there is shown a flow chart of a first embodiment of the biological sample observation method in accordance with the present invention, which is performed by using the biological sample observation system shown in FIG. 1.

In this embodiment of the biological sample observation method, the observation is performed by repeating a unitary observation process which sequentially performs a starting of the operation of the solid state image sensor, a starting of the observed image recording after lapse of a time $t_1$, a stopping of the observed image recording after lapse of a time $t_3$, a stopping of the operation of the solid state image sensor after lapse of a time $t_4$, and a waiting for a time time $t_6$. Accordingly, after lapse of a waiting time $t_6$, the operation of the solid state image sensor is started in a next unitary observation process.

The time $t_1$ is a wait time after the solid state image sensor is energized until an image is displayed. This time $t_1$ depends upon the type of the solid state image sensor and the type of the drive unit, but is preferred to be an appropriate value in the range of 1 second to 10 seconds.

The time $t_3$ is a period required for recording an observed image, and can be determined at an arbitrary value. However, the time $t_3$ is preferred to be as small as possible in order to reduce the influence of the heat generated from the solid state image sensor.

The time $t_4$ is a time after the recording of the observed image is stopped until the energization of the solid state image sensor is stopped. This time $t_4$ can be zero (0) so that the recording of the observed image is stopped at the same time as the energization of the solid state image sensor is stopped, or $t_4$ can be several seconds in order to smooth a joint between the recorded images of continuous periods.

The time $t_6$ is a time during which the solid state image sensor is maintained in a deenergized or non-operating condition. For a period of time $t_1 + t_3 + t_4$, the solid state image sensor is maintained in an operating condition, and therefore, heat is emitted from the solid state image sensor. On the other hand, for the time $t_6$, the heat generated during the period of time $t_1 + t_3 + t_4$ is dispersed. Therefore, the time $t_6$ has to be made sufficiently long for ensuring that the heat generated during the period of time $t_1 + t_3 + t_4$ is dispersed but is not accumulated in the sample. The time $t_6$ is preferred to be an appropriate value not less than 60 seconds.

Figure 5:
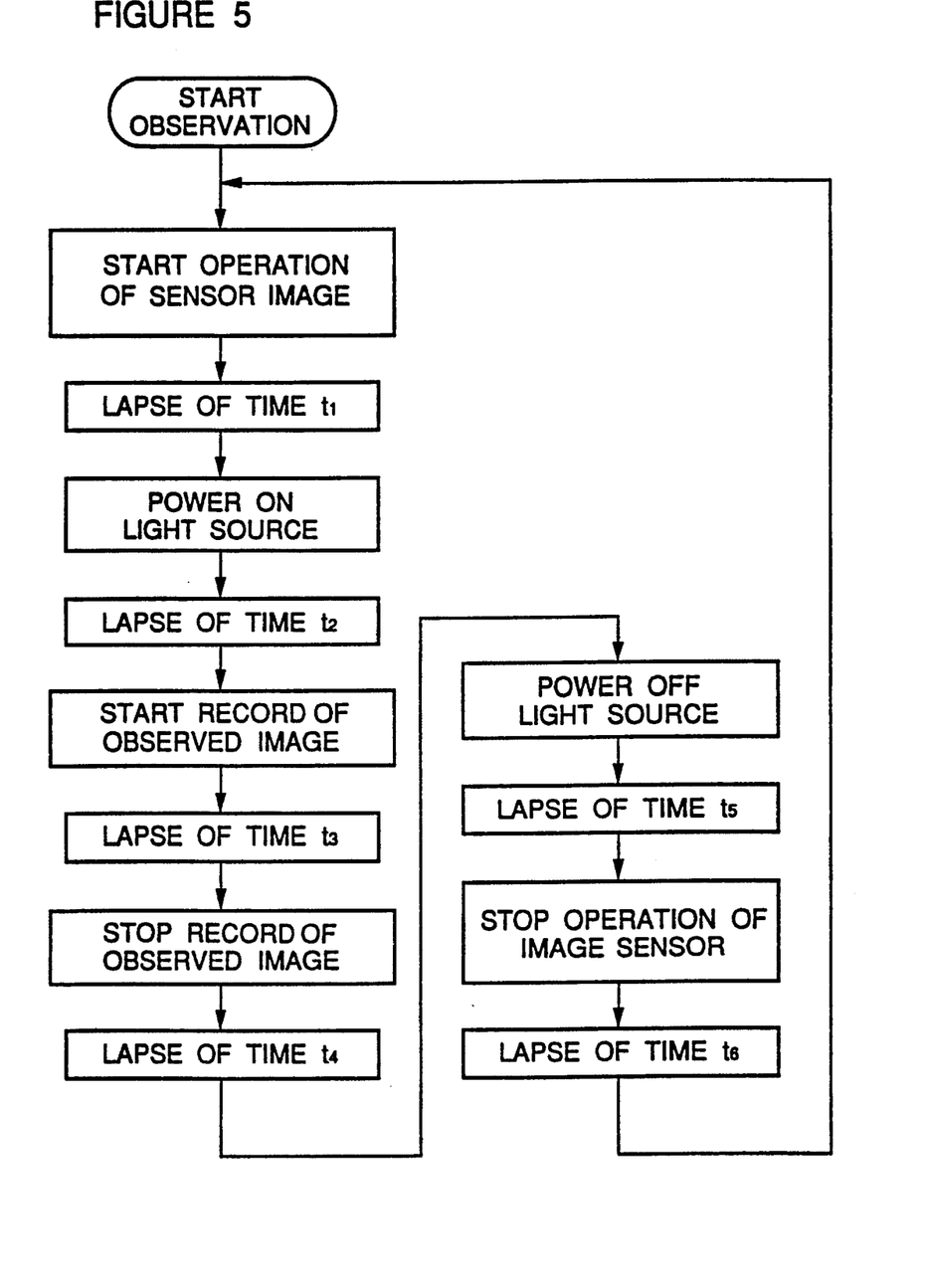
FIG. 5 is a flow chart of a second embodiment of the biological sample observation method in accordance with the present invention.

Referring to FIG. 5, there is shown a flow chart of a second embodiment of the biological sample observation method in accordance with the present invention, which is performed by using the biological sample observation system shown in FIG. 2.

In the second embodiment of the biological sample observation method, the observation is performed by repeating a unitary observation process which sequentially performs a starting of the operation of the solid state image sensor, a powering-on of the light source after lapse of a time $t_1$, a starting of the observed image recording after lapse of a time $t_2$, a stopping of the observed image recording after lapse of a time $t_3$, a powering-off of the light source after lapse of a time $t_4$, a stopping of the operation of the solid state image sensor after lapse of a time $t_5$, and a waiting for a time time $t_6$. Accordingly, after lapse of a waiting time $t_6$, the operation of the solid state image sensor is started in a next unitary observation process.

The time $t_2$ is a wait time after the light source is powered on until the light output of the light source becomes stable. Therefore, the time $t_2$ is preferred to be as small as possible, in order to avoid the temperature of the sample from being elevated by the heat generated by the light source. If there is used a light source such as a light emitting diode which stably emits a light immediately after energization or powering-on, the time $t_2$ can be made zero (0). However, if there is used a light source such as an incandescent electric lamp which needs some time after after energization or powering-on until a light output reaches a stable constant amount of light, the time $t_2$ is preferred to be on the order of a few seconds.

The time $t_5$ is a time after the light source is powered off until the operation of the solid state image sensor is stopped. This time $t_2$ can be zero (0) unless it is necessary to observe the sample under a special condition in which the observation is performed with no light irradiation.

The other times $t_1$, $t_3$, $t_4$ and $t_6$ are the same as the corresponding times of the first embodiment of the biological sample observation method.

In the first embodiment of the biological sample observation method shown in FIG. 4, the observed image is recorded for only the time $t_6$ for each unitary observation process time of $t_1 + t_3 + t_4 + t_6$, and in the second embodiment of the biological sample observation method shown in FIG. 5, the observed image is recorded for only the time $t_6$ for each unitary observation process time of $t_1 + t_2 + t_3 + t_4 + t_5 + t_6$. Embodiments are very desirable for the continuous observation, of the biological sample since the observed image of the constant time length is recorded without fail for every predetermined period.

Figure 6:
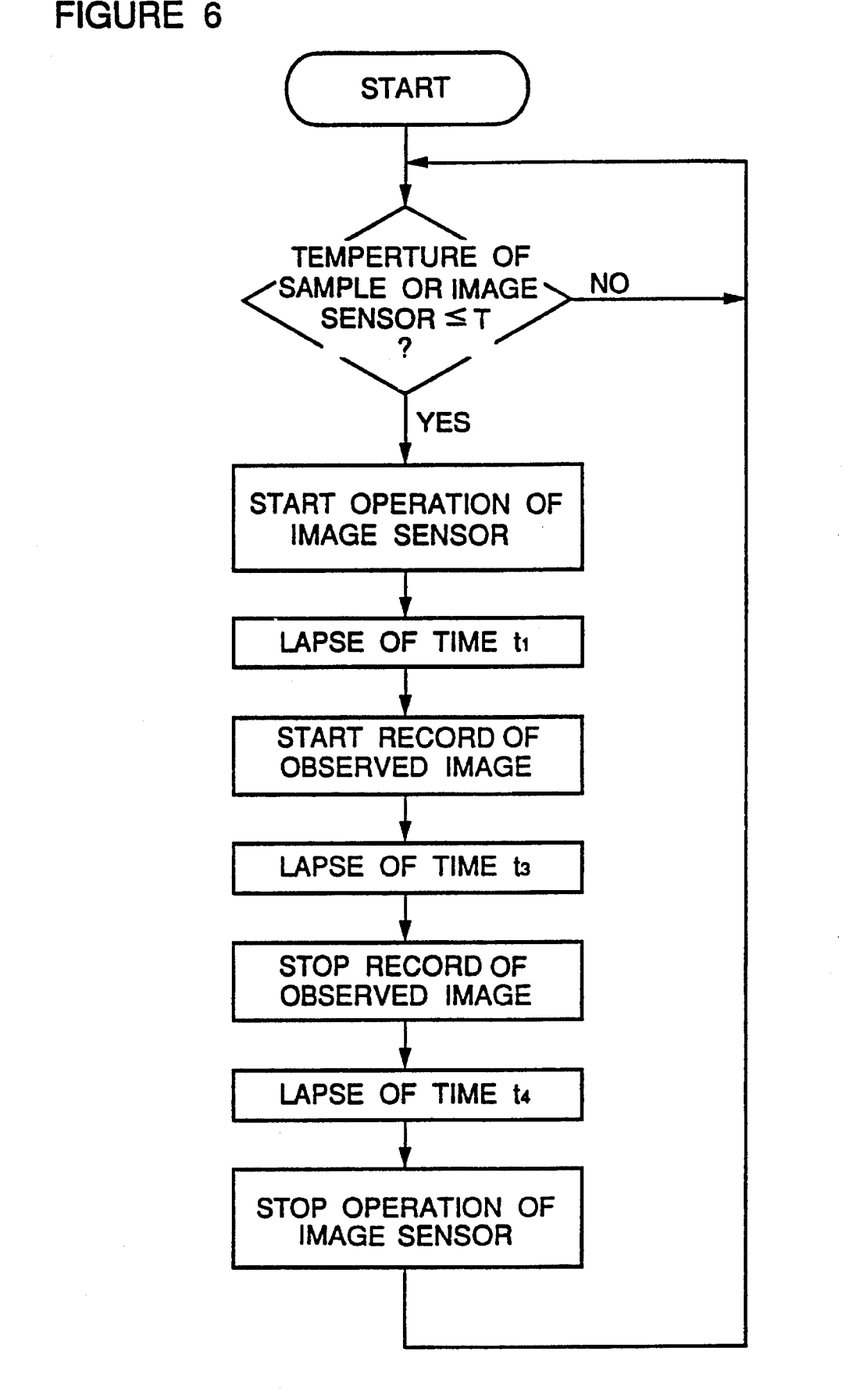
FIG. 6 is a flow chart of a third embodiment of the biological sample observation method in accordance with the present invention.

Referring to FIG. 6, there is shown a flow chart of a third embodiment of the biological sample observation method in accordance with the present invention, which is performed by using the biological sample observation system shown in FIG. 3.

In the third embodiment of the biological sample observation method, the observation is performed by repeating a unitary observation process which sequentially performs a starting of the operation of the solid state image sensor when the sample temperature or the surface temperature of the solid state image sensor is not greater than a predetermined reference temperature T, a starting of the observed image recording after lapse of a time $t_1$, a stopping of the observed image recording after lapse of a time $t_3$, and a stopping of the operation of the solid state image sensor after lapse of a time $t_4$.

The reference temperature T is determined at a temperature which dose not give any adverse thermal influence to the sample. If the holder 3 is located within the incubator so that the sample is observed while maintaining the sample temperature at a constant, the reference temperature T is determined at a temperature which is the same as a set temperature of the incubator or higher than the set temperature of the incubator by 1° C. Alternatively, if the sample temperature or the surface temperature of the solid state image sensor is measured before the sample observation is started, and then, the measured temperature can be used as the reference temperature T.

The times $t_1$, $t_3$ and $t_4$ are the same as the corresponding times of the first embodiment of the biological sample observation method.

In this third embodiment of the biological sample observation method, the intervals of the observed image recording are not necessarily at a constant. However, since the sample temperature is surely maintained around the reference temperature, a long continuous observation can be performed without adverse thermal influence to the sample.

For example, the biological sample observation systems shown in FIGS. 1 to 3 can be manufactured as follows: The sample observing part: including the solid state image sensor 2 and the drive unit 6 can be manufactured on the basis of a CCD monochrome camera available under the tradename TI-23A from NEC Corporation (Japan). The light source can be composed of an orange-colored light emitting diode available from Stanley Electric Co., Ltd. (Japan). The record and display unit 7 can be constituted of a time lapse videorecorder and a video display connected thereto. A personal computer can be used as the control unit 8. The temperature sensor 9 can be formed of a thermistor, so that control terminals of the drive unit and the videorecorder are switched on and off with reference to an output of the thermistor.

Reproduction of *Escherichia coli* was actually observed by the first embodiment of the biological sample observation method in accordance with the present invention by using the first embodiment of the biological sample observation system in accordance with the present invention and by locating the holder 3 (the sample observing part of the biological sample observation system) in an incubator of 37° C. The sample 1 was a plastic petri dish (Schale) including a nutrient agar depicted with a line pattern of *Escherichia coli*. In addition, the times $t_1$, $t_3$, $t_4$ and $t_6$ were set to be 5 seconds, 5 seconds, 1 second and 109 seconds, respectively.

Figure 7:
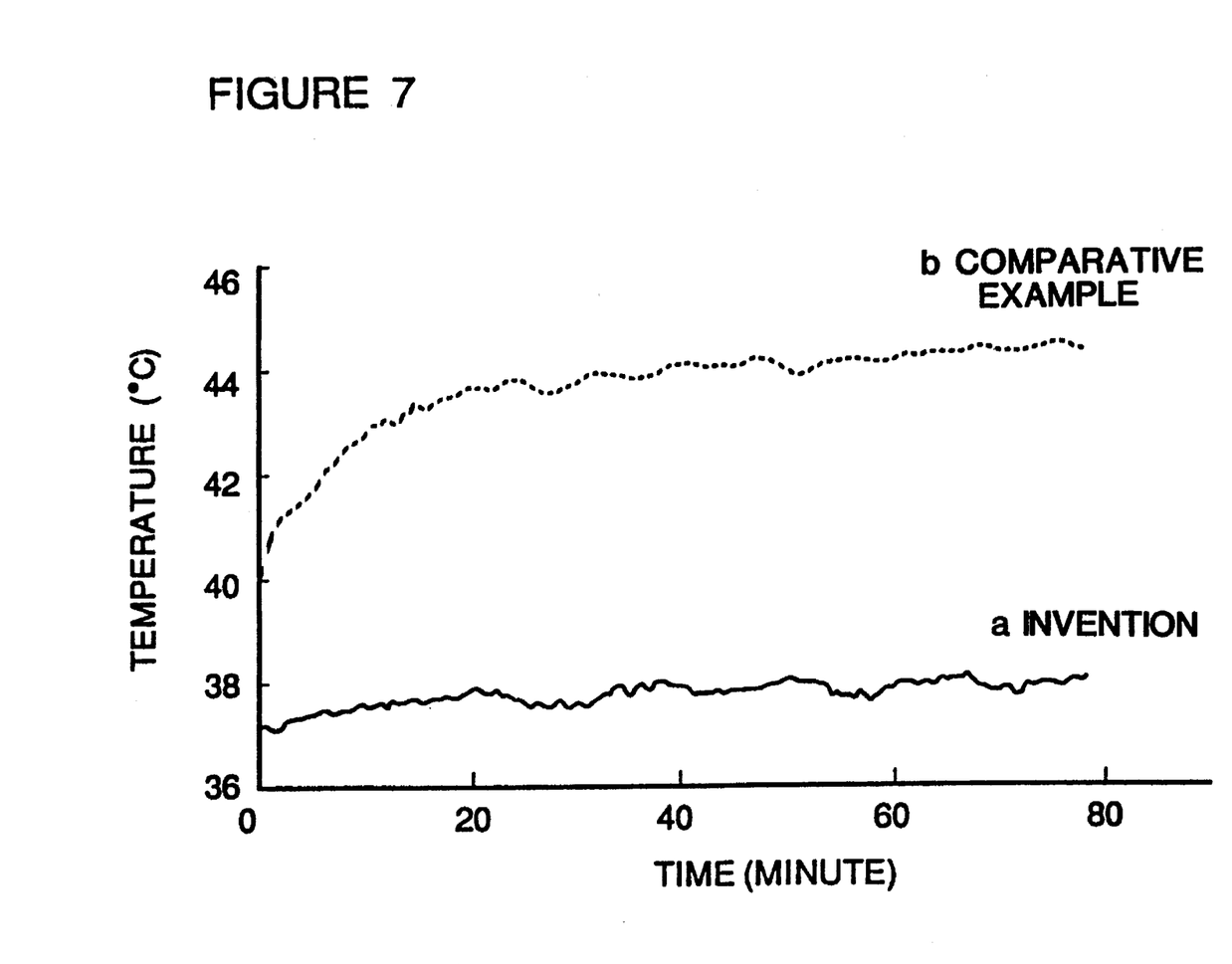
FIG. 7 is a graph illustrating the change over time of the surface temperature of the solid state image sensor when the first embodiment of the biological sample observation method in accordance with the present invention was performed by using the first embodiment of the biological sample observation system in accordance with the present invention.

FIG. 7 is a graph illustrating the change over time of the surface temperature of the solid state image sensor. The line "a" shows the change with time of the surface temperature of the solid state image sensor when the first embodiment of the biological sample observation method in accordance with the present invention was performed by using the first embodiment of the biological sample observation system in accordance with the present invention. Line "b" shows the change with time of the surface temperature of the solid state image sensor when the solid state image sensor was being continuously operated under the same condition. It should be noted that the elevation of the surface temperature of the solid state image sensor can be effectively prevented if the biological sample observation method in accordance with the present invention is performed.

Figure 8A:
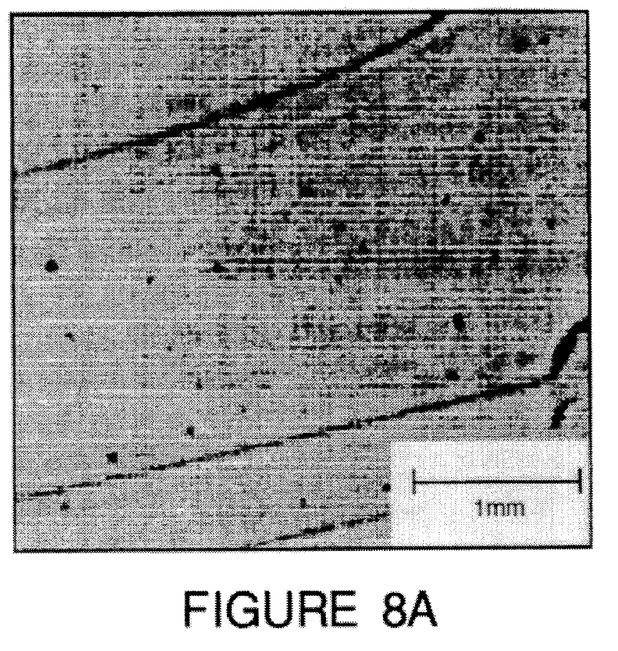
FIGS. 8A and 8B are photographs of *Escherichia coli* obtained by the first embodiment of the biological sample observation method in accordance with the present invention by using the first embodiment of the biological sample observation system in accordance with the present invention.
Figure 8B:
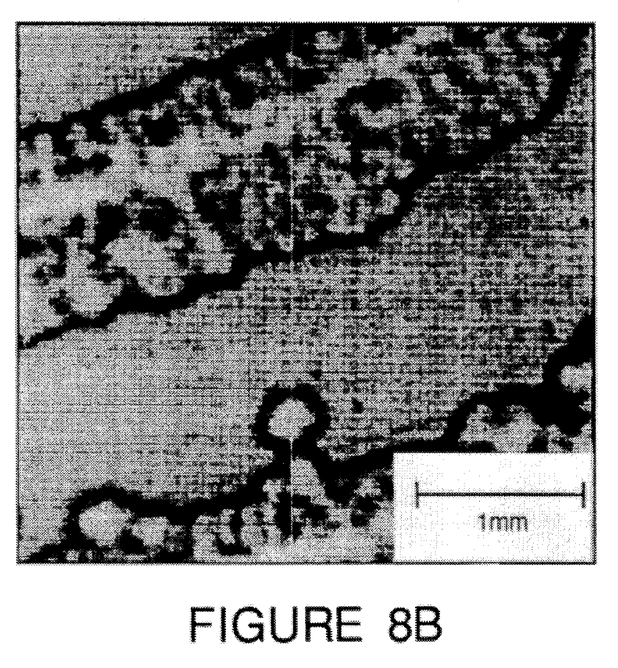

FIGS. 8A and 8B are photographs of *Escherichia coli* obtained by the first embodiment of the biological sample observation method in accordance with the present invention using the first embodiment of the biological sample observation system in accordance with the present invention. The photograph of FIG. 8A shows the state just after the observation was started, and the photograph of FIG. 8B shows the state when 12 hours have elapsed after the observation was started. Thus, the state of the growth of *Escherichia coli* was clearly observed.

As will be apparent from the above, if the biological sample observation method in accordance with the present invention and the biological sample observation system in accordance with the present invention are used, it is possible to effectively suppress or prevent the temperature elevation of the biological sample, which would otherwise be caused by the heat generated from the solid state image sensor and the light source. Accordingly, it is possible to continuously observe the growth of cultured cells or the reproduction of fungi or bacterium for a long time as they are, without giving adverse influence to the growth of cultured cells or the reproduction of fungi or bacterium.

The invention has thus been shown and described with reference to the specific embodiments. However, it should be noted that the present invention is in no way limited to the details of the illustrated structures but changes and modifications may be made within the scope of the appended claims.

I claim:

1. A biological sample observation system comprising a holding member in the form of a housing having a recess portion and a solid state area image sensor located in the recess portion, the holding member being configured to directly receive an object to be observed above a photoreception face of the solid state image sensor with no magnifying optical lens between the object to be observed and the photoreception face of the solid state image sensor, a light source located in the holding member for radiating light toward the photoreception face of the solid state image sensor through the object to be observed, a drive unit connected to the solid state image sensor for driving the solid state image sensor, a record and display unit connected to the drive unit for receiving through the drive unit observed image information picked up by the solid state image sensor, and a control unit connected to at least the drive unit for intermittently or periodically putting the solid state image sensor into an operating condition.

2. The biological sample observation system claimed in claim 1 wherein the control unit is connected to the light source for intermittently or periodically putting the light source and the solid state image sensor into an operating condition.

3. A biological sample observation system claimed in claim 1 further including a temperature sensor for measuring the temperature of the sample to be observed or the solid state image sensor, the control unit being also connected to the temperature sensor for controlling operation of at least the drive unit on the basis of an output of the temperature sensor.

4. A method for observing a biological sample using a sample holding member in the form of a housing having a recess portion and a solid state image sensor located in the recess portion, the holding member being configured to directly receive a biological sample to be observed above a photoreception face of the solid state image sensor with no magnifying optical lens between the biological sample to be observed and the photoreception face of the solid state image sensor, the method repeating the steps of driving the solid state image sensor, immediately starting to record in response to an output of the solid state image sensor, stopping the recording of the output of the solid state image sensor after the lapse of a predetermined period of time, immediately stopping the driving of the solid state image sensor, and allowing another predetermined period of time to elapse.

5. The method claimed in claim 4 and the added step wherein, when the solid state image sensor is driven, a light is immediately irradiated onto the photoreception face of the solid state image sensor, and when the driving of the solid state image sensor is stopped, the irradiation of the light onto the photoreception face of the solid state image sensor is immediately stopped.

6. A method for observing a biological sample using a sample holding member in the form of a housing having a recess portion and a solid state image sensor located in the recess portion, the holding member being configured to directly receive a biological sample to be observed above a photoreception face of the solid state image sensor with no magnifying optical lens between the biological sample to be observed and the photoreception face of the solid state image sensor, the method repeating a unitary observation process including the steps of driving the solid state image sensor when the temperature of the biological sample to be observed or the photoreception face of the solid state image sensor is not greater than a predetermined reference temperature, immediately starting to record an output of the solid state image sensor, stopping the recording of the output of the solid state image sensor after a lapse of a predetermined period of time, and immediately stopping the driving of the solid state image sensor.

7. A method for observing a biological sample using a sample holding member in the form of a housing having a recess portion and a solid state image sensor located in the recess portion, the holding member being configured to directly receive a biological sample to be observed above a photoreception face of the solid state image sensor with no magnifying optical lens between the biological sample to be observed and the photoreception face of the solid state image sensor, the method repeating the steps of driving the solid state image sensor, starting to record after a lapse of a first predetermined period of time following an output of the solid state image sensor, stopping the recording of the output of the solid state image sensor after the lapse of a second predetermined period of time, and stopping the driving of the solid state image sensor after a lapse of a third predetermined period of time.

8. The method claimed in claim 4 and the added step wherein, when the solid state image sensor is driven, a light is irradiated onto the photoreception face of the solid state image sensor after lapse of a fifth predetermined period of time, and when the driving of the solid state image sensor is stopped, the irradiation of the light onto the photoreception face of the solid state image sensor is stopped after lapse of a sixth predetermined period of time.

9. A method for observing a biological sample using a sample holding member in the form of a housing having a recessed portion and a solid state image sensor located in the recessed portion, the holding member being configured to directly receive a biological sample to be observed above a photoreception face of the solid state image sensor with no magnifying optical lens between the biological sample to be observed and the photoreception face of the solid state image sensor, the method repeating a unitary observation process including the steps of driving the solid state image sensor when the temperature of the biological sample to be observed or the photoreception face of the solid state image sensor is not greater than a second predetermined reference temperature, starting to record an output of the solid state image sensor after lapse of a first predetermined period of time, stopping the recording of the output of the solid state image sensor after a lapse of a second predetermined period of time, and stopping the driving of the solid state image sensor after lapse of a third predetermined period of time.

* * * * *